US012496152B2

(12) United States Patent
Yang

(10) Patent No.: US 12,496,152 B2
(45) Date of Patent: Dec. 16, 2025

(54) PUNCTURE GUIDING SYSTEM AND METHOD

(71) Applicant: National Taiwan University, Taipei (TW)

(72) Inventor: Shun-Mao Yang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 389 days.

(21) Appl. No.: 18/263,312

(22) PCT Filed: Jun. 7, 2021

(86) PCT No.: PCT/CN2021/098590
§ 371 (c)(1),
(2) Date: Jul. 27, 2023

(87) PCT Pub. No.: WO2022/256964
PCT Pub. Date: Dec. 15, 2022

(65) Prior Publication Data

US 2024/0415587 A1 Dec. 19, 2024

(51) Int. Cl.
*A61B 34/32* (2016.01)
*A61B 90/50* (2016.01)

(52) U.S. Cl.
CPC .............. *A61B 34/32* (2016.02); *A61B 90/50* (2016.02)

(58) Field of Classification Search
CPC ......... A61B 34/30; A61B 34/32; A61B 90/11; A61B 90/50
USPC .......................................................... 606/130
See application file for complete search history.

(56) References Cited

U.S. PATENT DOCUMENTS

| | | | |
|---|---|---|---|
| 2010/0233647 A1 | 9/2010 | Yang | |
| 2019/0133790 A1 | 5/2019 | Viscardi et al. | |
| 2020/0281676 A1 | 9/2020 | Rohs et al. | |

FOREIGN PATENT DOCUMENTS

| | | | | |
|---|---|---|---|---|
| CN | 110996826 A | 4/2020 | | |
| EP | 2508680 A1 | 10/2012 | | |
| GB | 2593741 A | * 10/2021 | ............ A61B 34/30 | |
| TW | 381008 B | 2/2000 | | |
| TW | I616192 B | 3/2018 | | |
| WO | 2021094448 A1 | 5/2021 | | |

* cited by examiner

*Primary Examiner* — Boniface N Nganga
(74) *Attorney, Agent, or Firm* — MUNCY, GEISSLER, OLDS & LOWE, P.C.

(57) ABSTRACT

A puncture guiding system and method are provided. The system includes a control device, a robotic arm, a diagnostic detection device, a screen, and a foot pedal. The method includes: installing the cannula on the robotic arm and placing the cannula on the patient's body; the diagnostic detection device scanning the patient to obtain a plurality of two-dimensional images; constructing a three-dimensional image; displaying the image on the screen; providing the foot pedal; according to the action of a switching button, the robotic arm switches between manual mode and fixed mode; setting a moving path of the cannula, and the screen displaying the movement trajectories; according to the activation of a first or a second moving button, the cannula moving to a first or a second position, and the screen displaying the movement trajectories. The invention enables the cannula to move more stably, slowly and safely.

20 Claims, 15 Drawing Sheets

PUNCTURE GUIDING SYSTEM AND METHOD

BACKGROUND OF THE INVENTION

1. Field of the Invention

The present invention relates generally to a puncture guiding system and method.

2. The Prior Arts

Techniques such as fine needle aspiration (FNA) biopy or percutaneous ablation usually need to be guided by diagnostic detection devices such as ultrasound or computed tomography (CT) before practitioners can determine the correct position of the cannula on the patient's body and the correct position of the needle on the cannula, and control the movement of the robotic arm through the control system. The robotic arm can control the cannula carrying the needle to move to the target to obtain tumor cells or complete ablation therapy.

Typically, the diagnostic testing device is near one end of the bed, and the robotic arm is near the side of the bed. The control system includes a table, a chair, an input device, an image capture device, and a screen. The chair is placed beside the table, the input device and the screen are located on the table, and the image capture device is put near the bed. The input device includes a computer, a keyboard, a mouse, a console, and a control panel. It is conceivable that except for the image capture device, the other components of the control system are arranged in groups, which are quite bulky and are not suitable to be installed on the side of the bed, otherwise the practitioners may be hindered by the bulky components from performing the operation.

However, if the practitioner is operating alone, after placing the cannula on the patient's body, the practitioner must walk from the side of the bed to the control system to confirm on the screen that the cannula is in the correct position.

Furthermore, if the practitioner is operating alone, after confirming that the cannula is placed in the correct position, the practitioner must walk from the side of the control system to the side of the bed to further manually move the position of the cannula to adjust the moving path of the cannula. After adjusting the moving path of the cannula, the practitioner must walk from the side of the bed to the control system to confirm on the screen whether the moving path of the cannula is correct. After confirming the moving path of the cannula, the practitioner can remotely control the robotic arm through the control system.

The problem with the above operation method is: first, the practitioners need to walk back and forth between the bed and the control system, which is time-consuming, laborious, and inefficient: second, the practitioners usually need to go through several corrections to adjust the moving path of the cannula, which is time-consuming and labor-intensive, and the efficiency is low.

In addition, the general robotic arm is usually fixed, and practitioners have no way to move the robotic arm arbitrarily.

Moreover, during walking, the practitioner's body is likely to collide with the robotic arm, causing the moving path of the cannula to deviate. Once the cannula moves on the deviated moving path, the needle on the cannula will excessively pull on the patient's wound.

In addition, the image capture device must constantly take pictures of the robot arm and send the photos to the computer, so that the computer can output the image of the real-time position of the robot arm to the screen, and the screen can display the moving trajectory of the robot arm and the cannula, which is costly and inefficient, as well as increases the patient's radiation exposure.

Finally, the average robotic arms tend to move too fast or too large, causing the needle on the cannula to bend or break, and excessively pulling on the patient's wound.

SUMMARY OF THE INVENTION

A primary objective of the present invention is to provide a puncture guiding system and method, wherein the cannula moves more stably, slowly and safely, and the movement accuracy of the robotic arm reaches millimeter level or less.

Another objective of the present invention is to provide a puncture guiding system and method, which can facilitate single-person bedside operation and observation of the position and moving trajectory of the robotic arm and cannula.

Another objective of the present invention is to provide a puncture guiding system and method, which can activate the robotic arm to be manually moved through a dual mechanism.

Yet another objective of the present invention is to provide a puncture guiding system and method, which is capable of sensing whether the robotic arm is impacted by an external force, and immediately controlling the robotic arm to stop moving.

A further objective of the present invention is to provide a puncture guiding system and method, which is capable of memorizing the real-time position of the robotic arm in space at any time, so as to calculate the target position of the robotic arm and set the moving path of the cannula.

Another objective of the present invention is to provide a puncture guiding system and method, which is capable of controlling the low-speed movement of the robotic arm.

For achieving the foregoing objectives, the present invention provides a puncture guiding system, comprising: a control device, a robotic arm, a diagnostic detection device, a screen, and a foot pedal. The control device has an image reconstruction module. The robotic arm is electrically connected to the control device, has a manual mode and a fixed mode, and is disposed with a cannula, which is to be placed at a first position a patient's body. The diagnosis detection device is electrically connected to the control device to scan the patient's body to obtain a plurality of two-dimensional (2D) images of the cannula and tissues near the first position. The image reconstruction module receives the plurality of 2D images and constructs a three-dimensional (3D) image. The screen is electrically connected to the control device, receives and displays the plurality of 2D images, 3D images, or a combination thereof. The foot pedal is electrically connected to the control device and includes a switching button, a first moving button, and a second moving button; wherein the control device controls the robotic arm to switch to the manual mode or the fixed mode according to the actuation of the switching button: wherein, in the manual mode, the robotic arm is manually moved to adjust the position of the cannula to a second position, and the control device sets the path between the first position and the second position as a moving path of the cannula: wherein, in the fixed mode, the control device controls the robotic arm to move according to the actuation of the first moving button to drive the cannula to move from the second position to the first position along the moving path, and the control device moves the cannula from the second position to the first position along the moving path according to the actuation of the second moving button, wherein the screen displays the movement trajectories of the robotic arm and the cannula.

In some embodiments, the image reconstruction module defines a spatial relationship between the cannula and a target object according to the plurality of 2D images and constructs a 3D image: when the cannula is at the first position, an axis of the cannula and an axis of the target object are not aligned; when the cannula is at the second position, the axis of the cannula is aligned with the axis of the target object.

In some embodiments, when the switching button is activated, the foot pedal transmits a first switching signal to the control device, and the control device controls the robotic arm to switch to the manual mode according to the first switching signal.

In some embodiments, when the switching button is not activated, the foot pedal transmits a second switching signal to the control device, and the control device controls the robotic arm to switch to the fixed mode according to the second switching signal.

In some embodiments, in the fixed mode, when the first moving button is activated and the second moving button is not activated, the foot pedal transmits a first moving signal to the control device, the control device controls the movement of the robotic arm according to the first moving signal, the robotic arm drives the cannula to move from the second position to the first position along the moving path, and the screen displays the movement trajectories of the robotic arm and the cannula.

In some embodiments, in the fixed mode, when the second moving button is activated and the first moving button is not activated, the foot pedal transmits a second moving signal to the control device, the control device controls the movement of the robotic arm according to the second moving signa, the robotic arm drives the cannula to move from the first position to the second position along the moving path, and the screen displays the movement trajectories of the robotic arm and the cannula.

In some embodiments, the puncture guiding system further comprises a force sensor, disposed on the robotic arm and electrically connected to the control device; wherein, when the robotic arm switches to manual mode and the force sensor detects that the robotic arm is manually moved, the force sensor sends a first sensing signal to the control device, and the control device controls the robotic arm to be manually moved according to the first sensing signal.

In some embodiments, the puncture guiding system further comprises a force sensor, disposed on the robotic arm and electrically connected to the control device; wherein, when the robotic arm switches to the fixed mode and the force sensor senses that the robotic arm is impacted by an external force, the force sensor sends a second sensing signal to the control device, and the control device controls the robotic arm to stop moving according to the second sensing signal.

In some embodiments, the puncture guiding system further comprises a register disposed on the robotic arm and electrically connected to the control device; wherein, when the robotic arm switches to manual mode, the register stores a real-time spatial position of the robotic arm, the control device recalculates a moving target position of the robotic arm according to the real-time spatial position of the robotic arm provided by the register, so as to set the moving path of the cannula, and the movement trajectories of the robotic arm and the cannula are displayed on the screen.

In some embodiments, in the fixed mode, a moving speed of the robotic arm is 0.2-1 cm per second in the fixed mode.

In order to achieve the aforementioned objectives, the present invention provides a puncture guiding method, comprising the following steps: controlling a robotic arm to drive a cannula to be placed at a first position on a patient's body, the cannula being installed on the robotic arm: providing a diagnostic detection device to scan the patient's body to obtain a plurality of 2D images of the cannula and tissues near the first position: constructing a 3D image based on the plurality of 2D images; providing a screen to display the plurality of 2D images and 3D images, or any combination of both: providing a foot pedal, the foot pedal comprising: a switching button, a first moving button, and a second moving button: according to the activation of the switching button, controlling the robotic arm to switch to a manual mode or a fixed mode: in the manual mode, the robotic arm being manually moved to adjust the position of the cannula to a second position, and the path between the first position and the second position being defined as a moving path of the cannula, and the screen displaying the movement trajectories of the cannula and the robotic arm; in the fixed mode, according to the activation of the first moving button, controlling the movement of the robotic arm to drive the cannula to move from the second position to the first position along the moving path, and the screen displaying the movement trajectories of the robotic arm and the cannula; and in the fixed mode, according to the activation of the second moving button, controlling the movement of the robotic arm to drive the cannula to move from the first position to the second position along the moving path, and the screen displaying the movement trajectories of the robotic arm and the cannula.

In some embodiments, the image reconstruction module defines a spatial relationship between the cannula and a target object according to the plurality of 2D images and constructs a 3D image: when the cannula is at the first position, an axis of the cannula and an axis of the target object are not aligned: when the cannula is at the second position, the axis of the cannula is aligned with the axis of the target object.

In some embodiments, when the switching button is activated, the foot pedal transmits a first switching signal to a control device, and the control device controls the robotic arm to switch to the manual mode according to the first switching signal.

In some embodiments, when the switching button is not activated, the foot pedal transmits a second switching signal to a control device, and the control device controls the robotic arm to switch to the fixed mode according to the second switching signal.

In some embodiments, in the fixed mode, when the first moving button is activated and the second moving button is not activated, the foot pedal transmits a first moving signal to a control device, the control device controls the movement of the robotic arm according to the first moving signal, the robotic arm drives the cannula to move from the second position to the first position along the moving path, and the screen displays the movement trajectories of the robotic arm and the cannula.

In some embodiments, in the fixed mode, when the second moving button is activated and the first moving button is not activated, the foot pedal transmits a second moving signal to a control device, the control device controls the movement of the robotic arm according to the second moving signa, the robotic arm drives the cannula to move from the first position to the second position along the moving path, and the screen displays the movement trajectories of the robotic arm and the cannula.

In some embodiments, when the robot arm is switched to the manual mode and a force sensor detects that the robot arm is manually moved, the force sensor sends a first sensing signal to the control device, and the control device controls the robotic arm to be moved manually according to the first sensing signal.

In some embodiments, when the robotic arm switches to the fixed mode and a force sensor detects that the robotic arm is impacted by an external force, the force sensor sends a second sensing signal to the control device, and the control device controls the robot arm to stop moving according to the second sensing signal.

In some embodiments, when the robotic arm is switched to the manual mode, a register stores the real-time spatial position of the robotic arm, and the control device recalculates the moving target position of the robotic arm according to the real-time spatial position of the robotic arm provided by the register, so as to set the moving path of the cannula, and the movement trajectories of the robotic arm and the cannula are displayed on the screen.

In some embodiments, in the fixed mode, a moving speed of the robotic arm is 0.2-1 cm per second.

The effect of the present invention is that the present invention can control the robotic arm through the foot pedal, the movement of the cannula is relatively stable, slow and safe, and the movement accuracy of the robotic arm reaches the millimeter level or less, and the cannula can move along the moving path to the destination without deviation.

Furthermore, the present invention can facilitate a practitioner to operate alone the entire surgical process such as fine needle puncture, scanning, and setting the moving path, and at the same time observe the position and movement trajectories of the robotic arm and cannula on the screen, and control the robotic arm by stepping on the foot pedal. As such, the practitioner can free up both hands to do things, save time and effort, achieve high operating efficiency, and save labor costs.

In addition, the present invention can activate the robotic arm through the dual mechanisms of the foot pedal and the force sensor, so that the robotic arm can be manually moved, thereby improving the operation safety.

Moreover, the present invention can detect whether the robotic arm is impacted by an external force in a fixed mode through the force sensor, and immediately control the robotic arm to stop moving, preventing the cannula from moving on the deviated path and causing the cannula to making the needle excessively pulls on the patient's wound.

Furthermore, the present invention can store the real-time spatial position of the robot arm at any time through the register to calculate the moving target position of the robot arm, and set the moving path of the cannula, as well as cooperate with the screen to display the movement trajectories of the robot arm and the cannula. While standing on the bedside and controlling the robotic arm by stepping on the foot pedal, the practitioner can observe on the screen whether the position of the cannula and the moving path are correct. As such, the practitioner can easily move the cannula to the correct position in one step, without repeated corrections, and the operation efficiency is high, and there is no need to install an additional image capture device and employ another person to assist in the operation: thereby, saving costs and reducing unnecessary radiation exposure for the patients.

In addition, the present invention can limit the movement of the robotic arm at a low speed in a fixed mode, which not only prevents the needle on the cannula from being bent or broken, but also avoids excessive pulling on the patient's wound.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
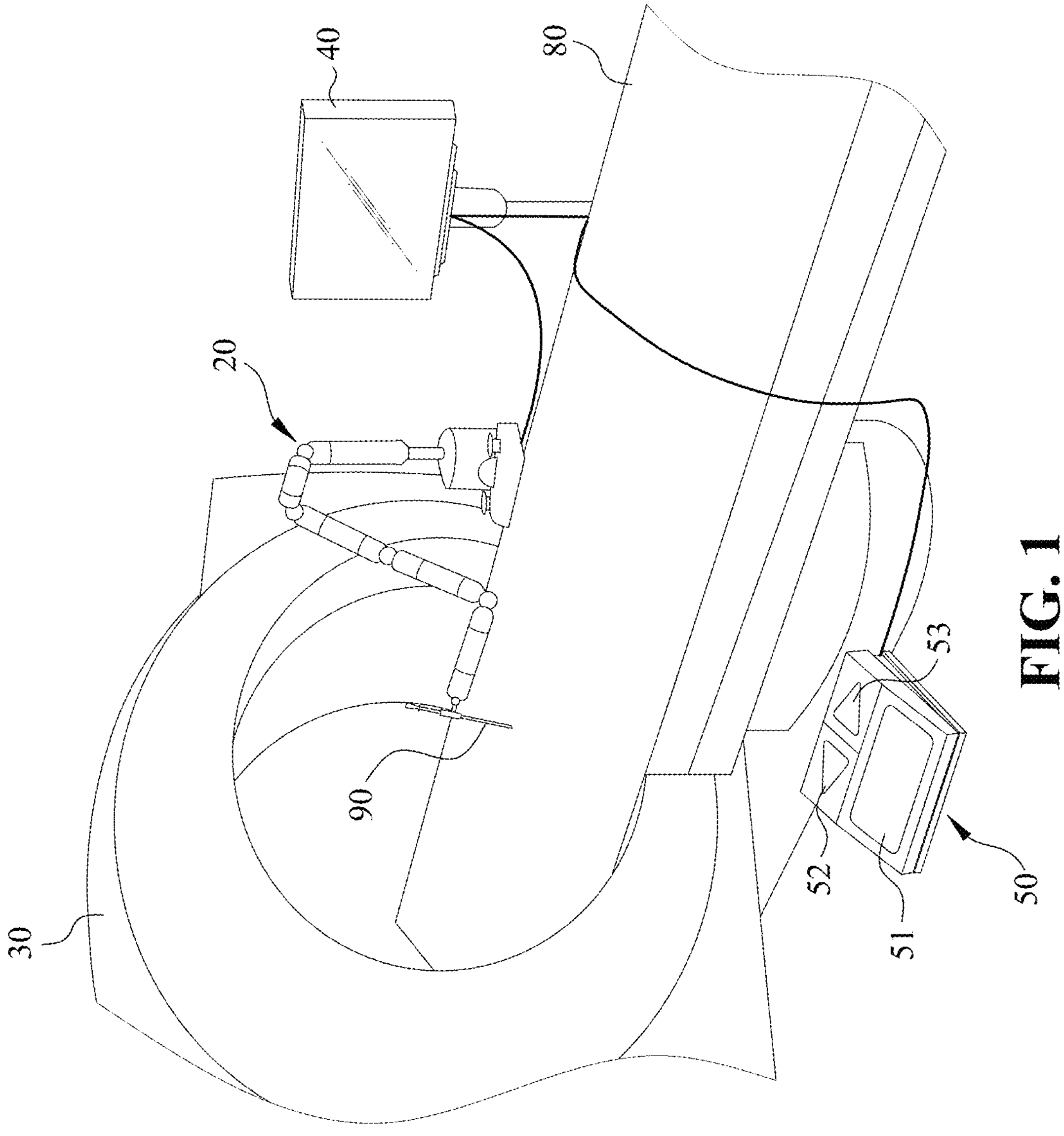
FIG. 1 is a perspective view of a puncture guiding system of the present invention.
Figure 2:
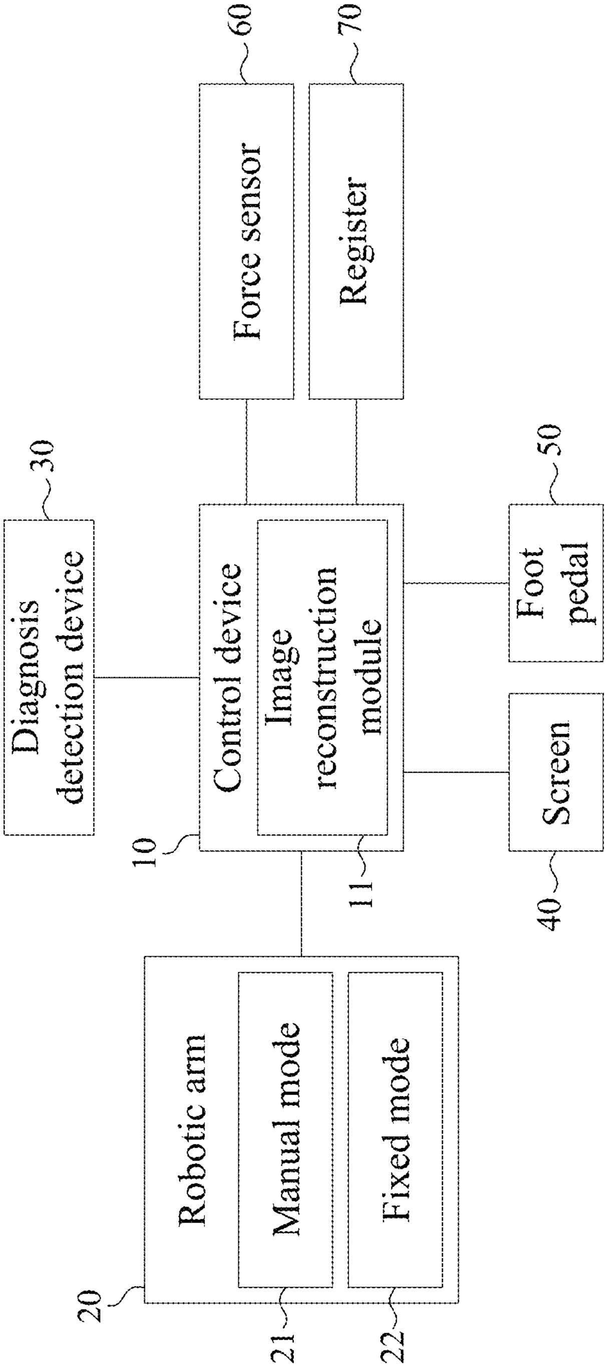
FIG. 2 is a schematic structural view of the puncture guiding system of the present invention.

Refer to FIG. 1 and FIG. 2. The present invention provides a puncture guiding system, including a control device 10, a robotic arm 20, a diagnostic detection device 30, a screen 40, a foot pedal 50, a force sensor 60, and a register 70. The control device 10 has an image reconstruction module 11. The robotic arm 20 is located on a first side of a bed 80, is electrically connected to the control device 10, has a manual mode 21 and a fixed mode 22, and is disposed with a cannula 90. The diagnostic detection device 30 is located at a first end of the bed 80 and is electrically connected to the control device 10. The screen 40 is located on the first side of the bed 80 and is electrically connected to the control device 10. The foot pedal 50 is located on a second side of the bed 80, is electrically connected to the control device 10, and includes a switching button 51, a first moving button 52, and a second moving button 53. The force sensor 60 is disposed on the robot arm 20 and electrically connected to the control device 10. The register 70 is disposed on the robot arm 20 and electrically connected to the control device 10.

Figure 3:
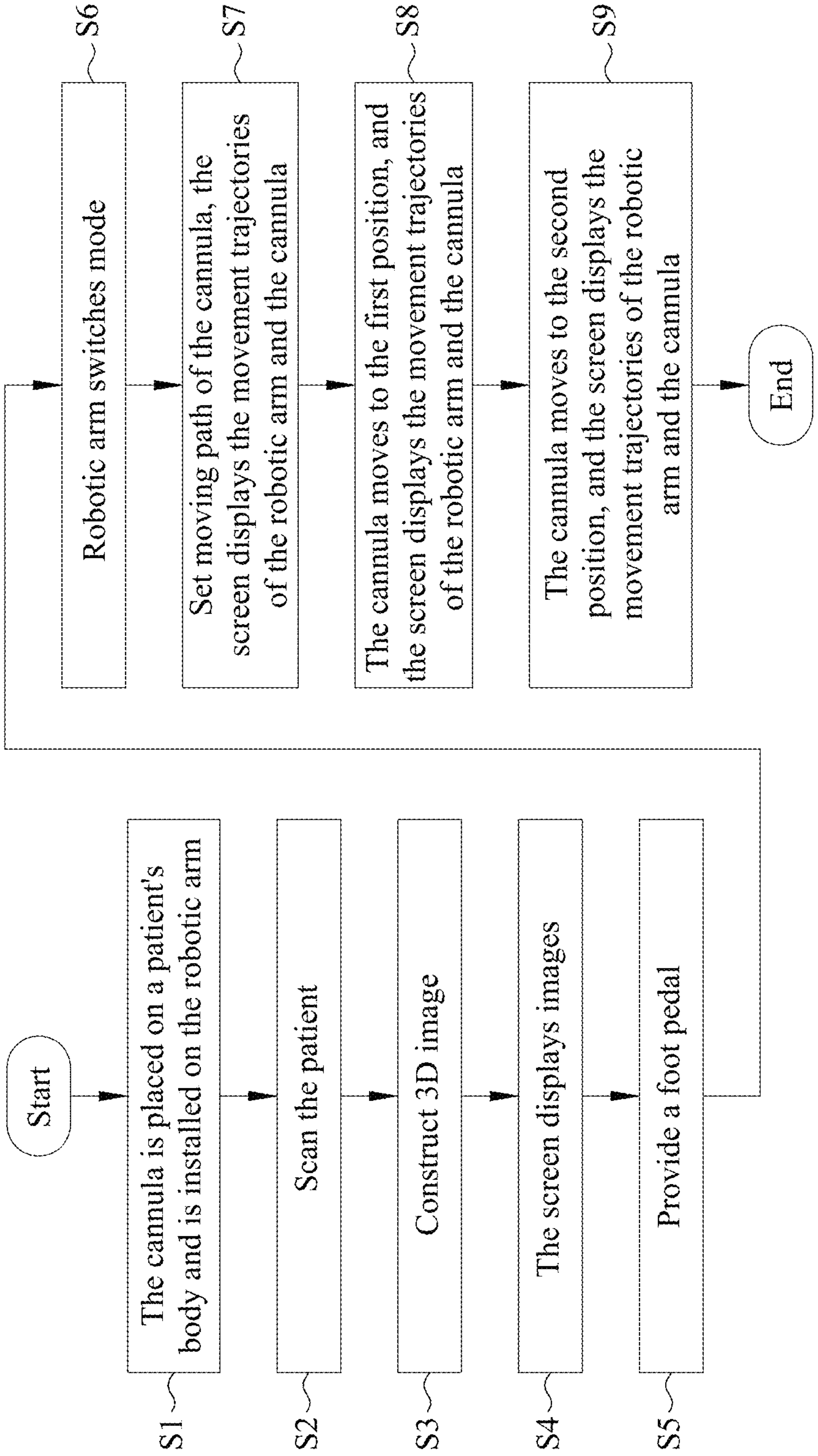
FIG. 3 is a flow chart of a puncture guiding method of the present invention.
Figure 4:
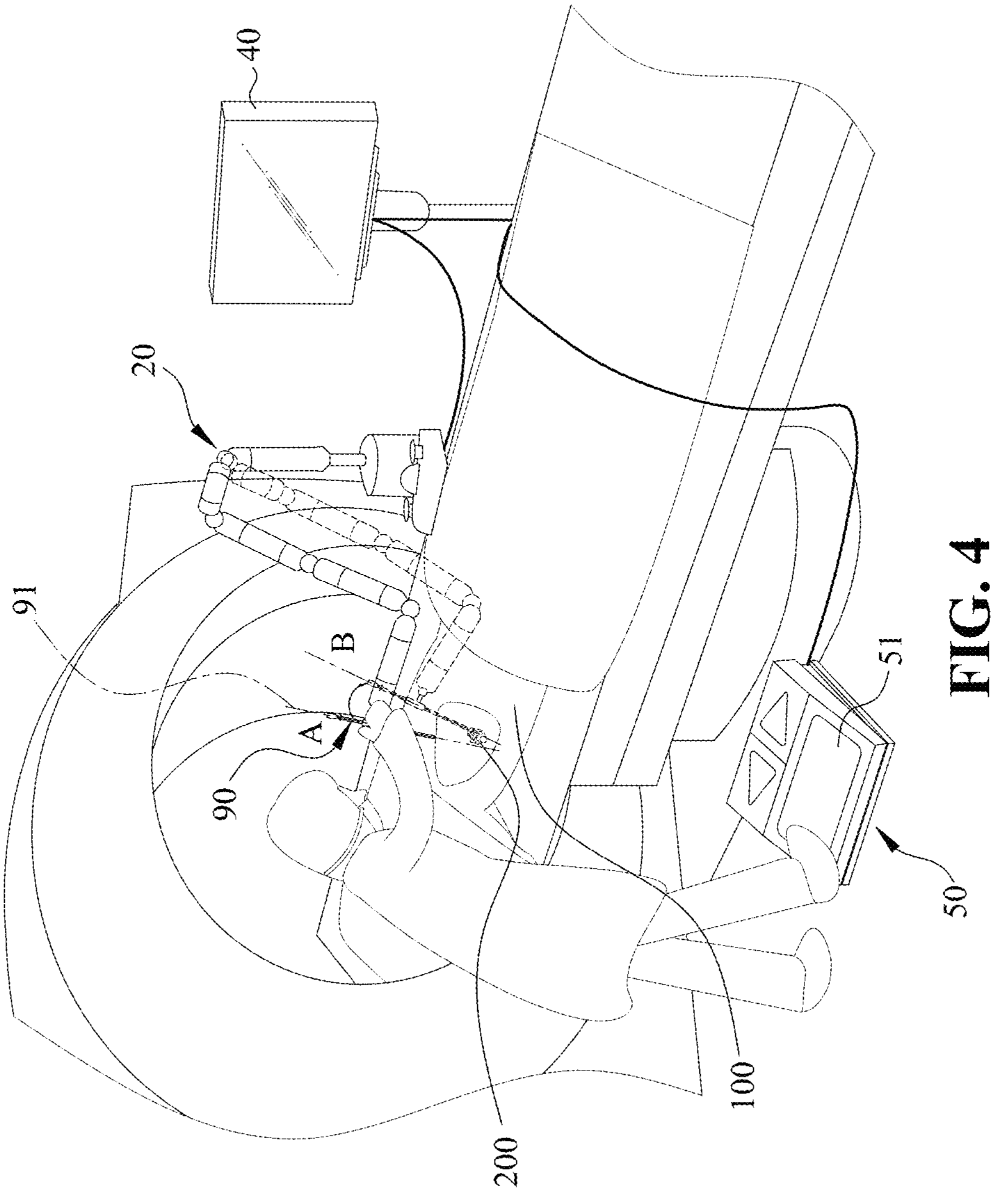
FIG. 4 is a schematic view of step S1 of the puncture guiding method of the present invention.

Referring to FIG. 3 to FIG. 14, the present invention provides a puncture guiding method, which includes the following steps:

Step S1 is to, as shown in FIG. 3 and FIG. 4, control the robotic arm 20 to drive the cannula 90 to a first position A on the body of a patient 100, and the cannula 90 is installed on the robotic arm 20.

In step S2, as shown in FIG. 3, and FIG. 5 to FIG. 7, a diagnostic detection device 30 is provided to scan the body of the patient 100 to obtain a plurality of 2D images 31 of the cannula 90 and tissues near the first position A. More specifically, the tissue near the first position A includes a target object 200 and the tissue around the target object 200. The target object 200 can be any tissue in the patient's body, such as a tumor.

Figure 7:
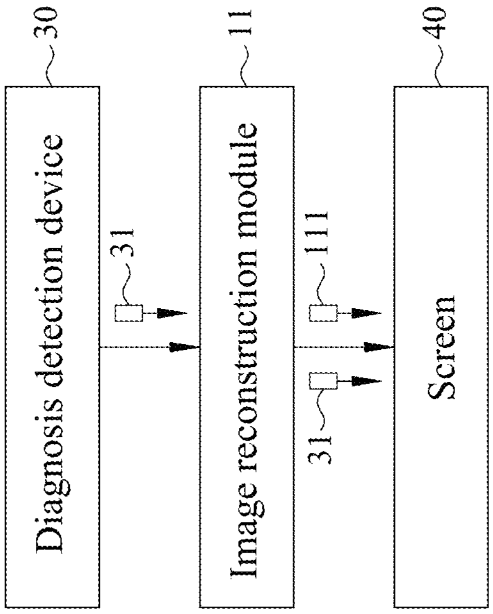
FIG. 7 is a schematic structural view of image conversion and output in the present invention.

Step S3 is to, as shown in FIG. 3 and FIG. 7, construct a 3D image 111 according to the plurality of 2D images 31.

Figure 8:
FIG. 8 is a schematic diagram of the screen displaying the cannula and the 2D and 3D images near the first position of the present invention.

Step S4 is to, as shown in FIG. 3, FIG. 7, and FIG. 8, provide a screen 40 to display the plurality of 2D images 31, 3D images 111, or a combination thereof. FIG. 8 shows a 3D image 111 at the lower right of the screen 40, and FIG. 8 shows a 2D image 31 at the upper left, lower left, and upper right of the screen 40. In other embodiments, the screen 40 can display only the 2D image 31 or the 3D image 111.

In step S5, as shown in FIG. 1 and FIG. 3, a foot pedal 50 is provided, and the foot pedal 50 includes a switching button 51, a first moving button 52, and a second moving button 53.

Figure 9:
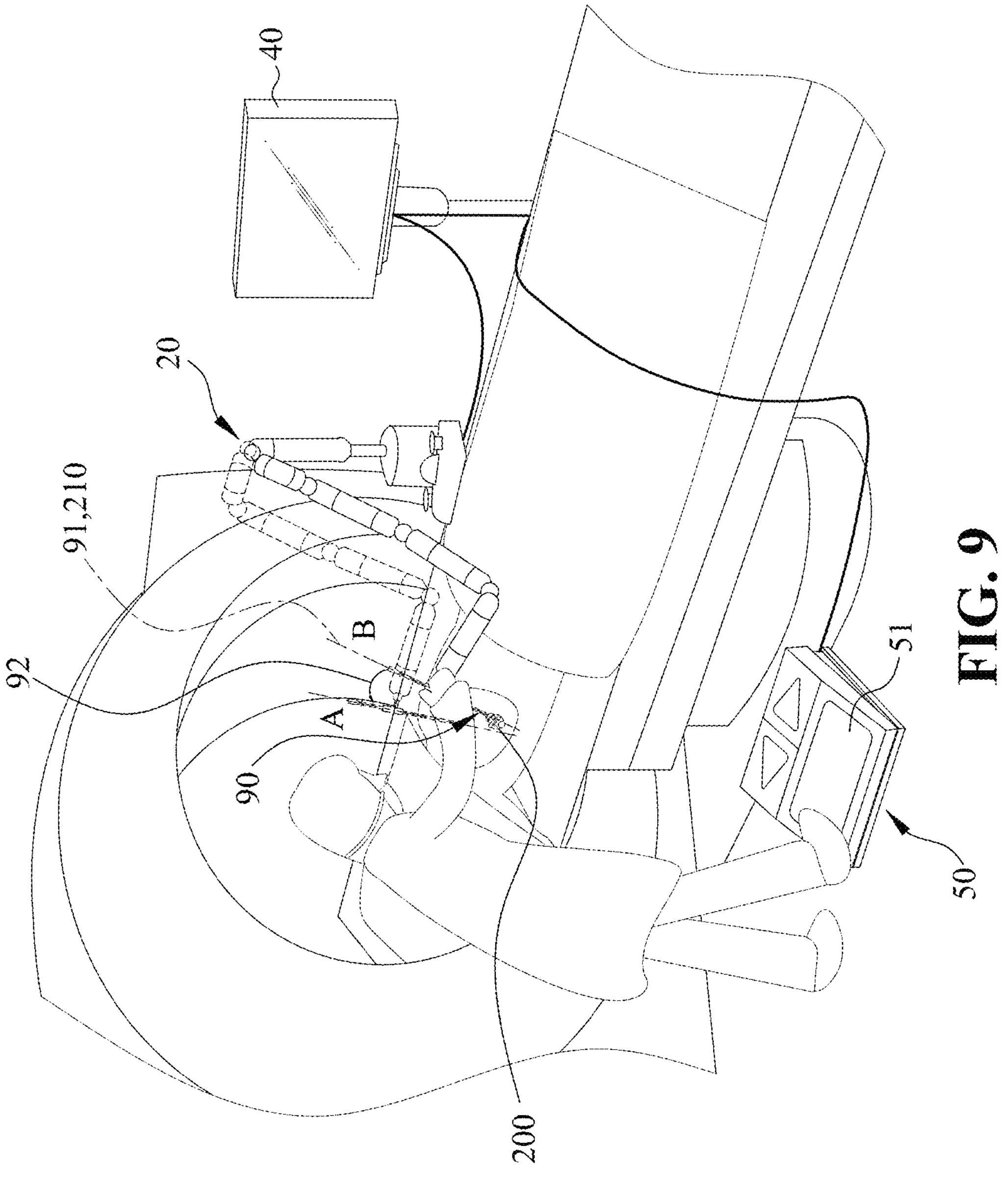
FIG. 9 is a schematic view of the operation of the robotic arm of the present invention in a manual state.
Figure 10:
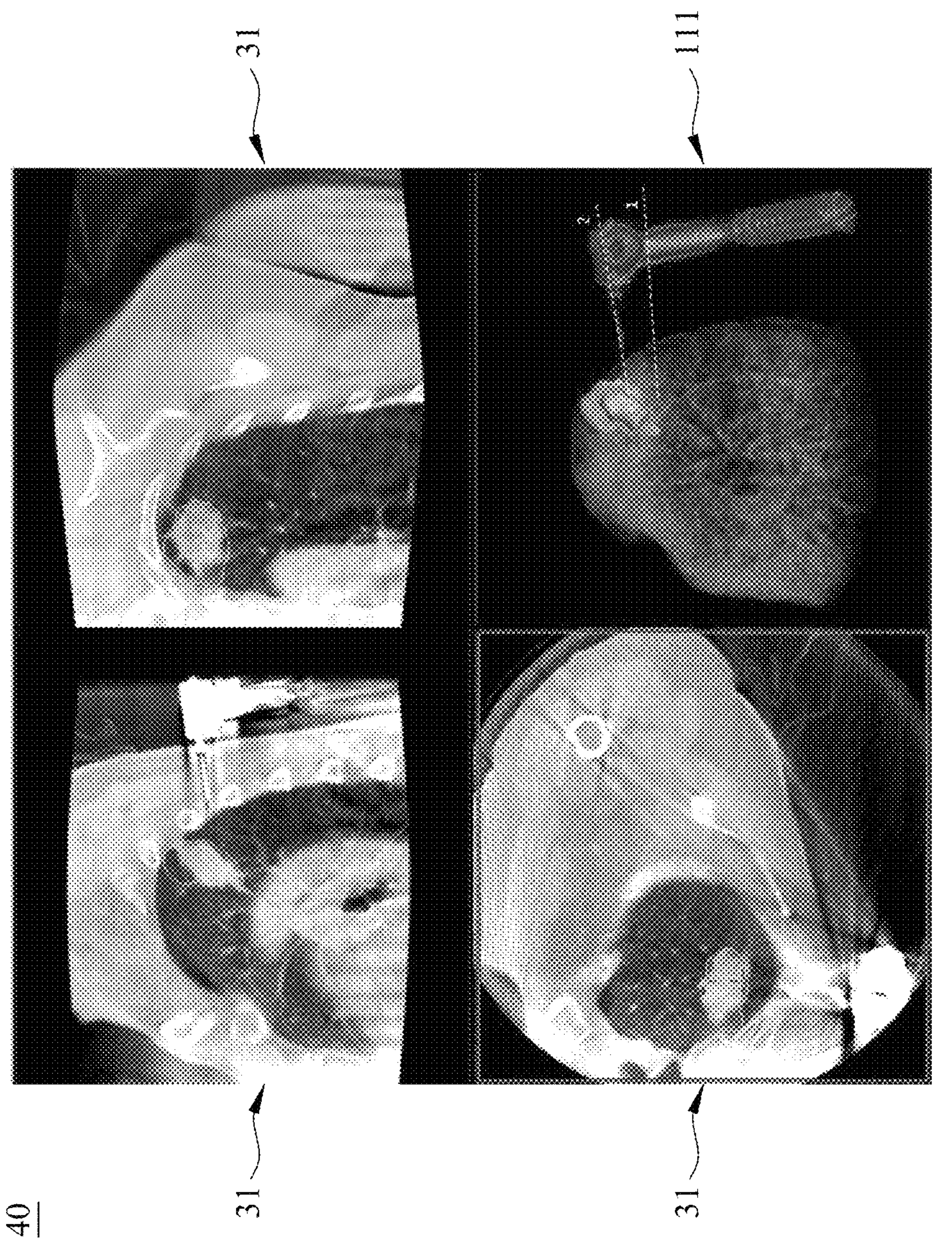
FIG. 10 is a schematic diagram of the screen displaying the cannula and the 2D and 3D images in the vicinity of the second position of the present invention.

Step S6 is to, as shown in FIG. 3 and FIG. 9, control the robotic arm 20 to switch to the manual mode 21 or the fixed mode 22 according to the activation of the switching button 51.

In step S7, as shown in FIG. 3, and FIG. 9 to FIG. 12, in the manual mode 21, the robotic arm 20 is manually moved to adjust the position of the cannula 90 to a second position B, and a path between the first position A and the second position B is set as a moving path 92 of the cannula 90, and the screen 40 displays the movement trajectories of the robot arm 20 and the cannula 90.

Figure 13:
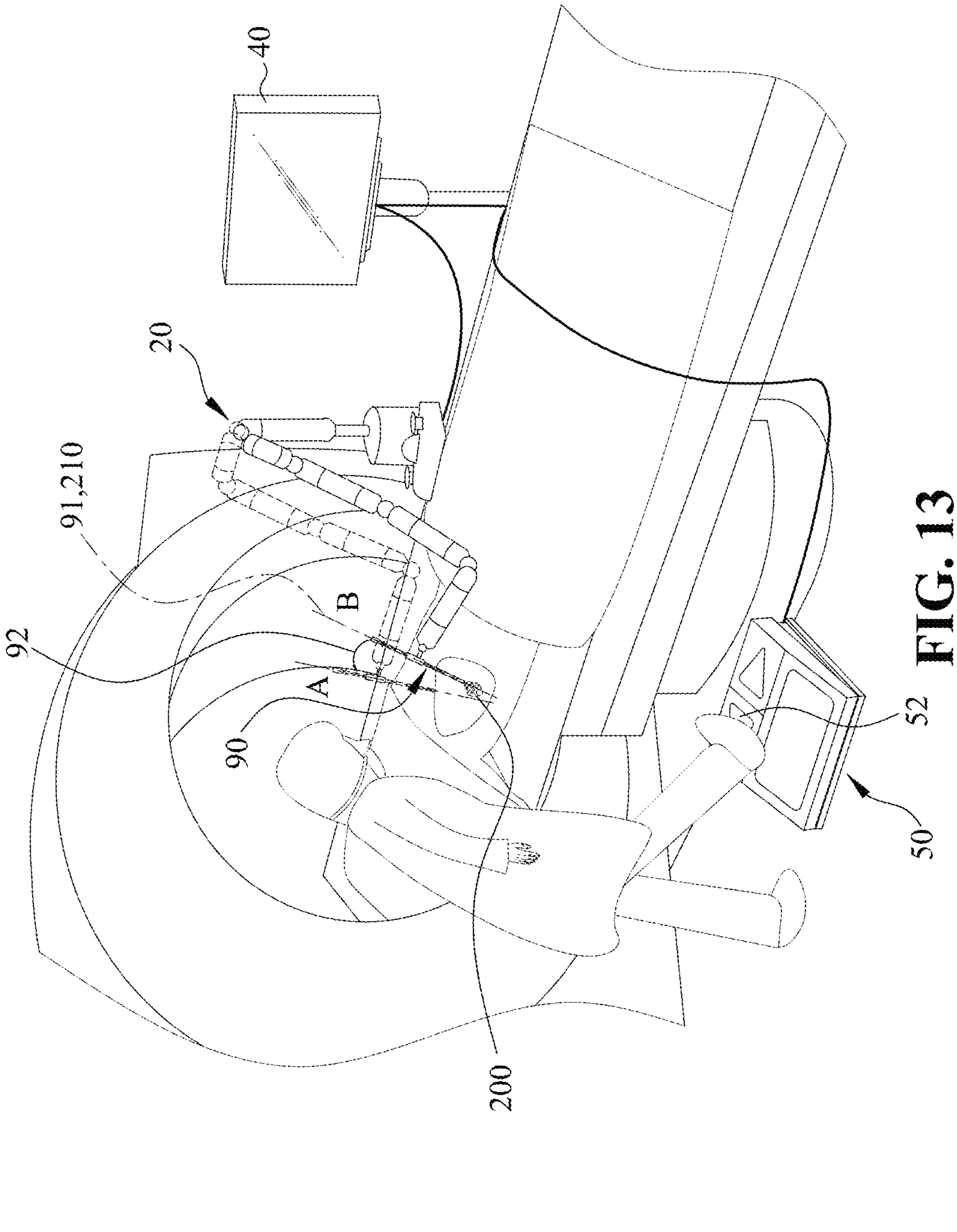
FIG. 13 is a schematic view of the robotic arm driving the cannula to move from the second position to the first position along the moving path of the present invention.

Step S8 is to, as shown in FIG. 3 and FIG. 13, in the fixed mode 22, according to the activation of the first moving button 52, control the movement of the robotic arm 20 and drive the cannula 90 along the moving path 92 from the second position B to the first position A, the screen 40 displays the movement trajectories of the robot arm 20 and the cannula 90.

Figure 14:
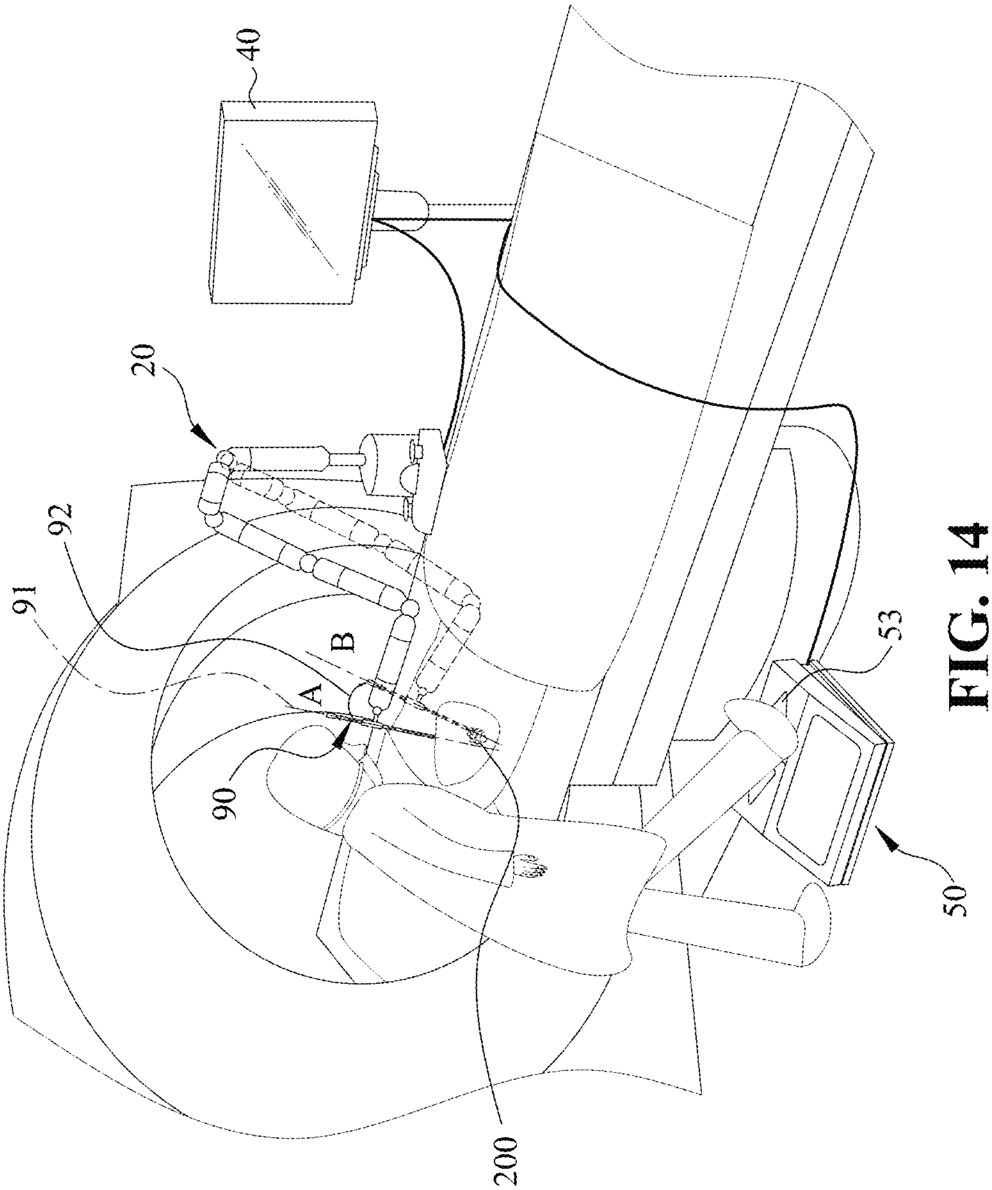
FIG. 14 is a schematic view of the robotic arm driving the cannula to move from the first position to the second position along the moving path of the present invention.

In step S9, as shown in FIG. 3 and FIG. 14, in the fixed mode 22, according to the activation of the second moving button 53, the movement of the robotic arm 20 is controlled to drive the cannula 90 along the moving path 92 from the first position A to the second position B, the screen 40 displays the movement trajectories of the robot arm 20 and the cannula 90.

As such, the present invention can control the robotic arm 20 through the foot pedal 50, the movement of the cannula 90 is relatively stable, slow and safe, the movement accuracy of the robotic arm 20 reaches the millimeter level or less, and the cannula 90 can be moved very precisely along the moving path 92 to the target position without deviation.

Furthermore, step S1 actually has two operation modes. Regarding the first mode of operation, the cannula 90 is first installed on the robotic arm 20, and then the switching button 51 is stepped on to switch the robotic arm 20 to the manual mode 21. At this point, the practitioner can manually move the robotic arm 20, so that the cannula 90 is placed at a first location A on the body of the patient 100. Regarding the second mode of operation, the cannula 90 is first placed at the first position A of the body of the patient 100, and then the switching button 51 is stepped with the foot, so that the robotic arm 20 is switched to the manual mode 21. At this point, the practitioner can manually move the robotic arm 20 to beside the cannula 90, and finally install the cannula 90 on the robotic arm 20.

As shown in FIG. 1, in a preferred embodiment, the diagnostic detection device 30 is a computed tomography scanner that senses the cannula 90 through an image segmentation algorithm (for example, a histogram method or a level set method). Therefore, the 2D image 31 is a 2D slice image generated by a computed tomography scanner, and is output to the image reconstruction module 11 in the format of DICOM.

Figure 5:
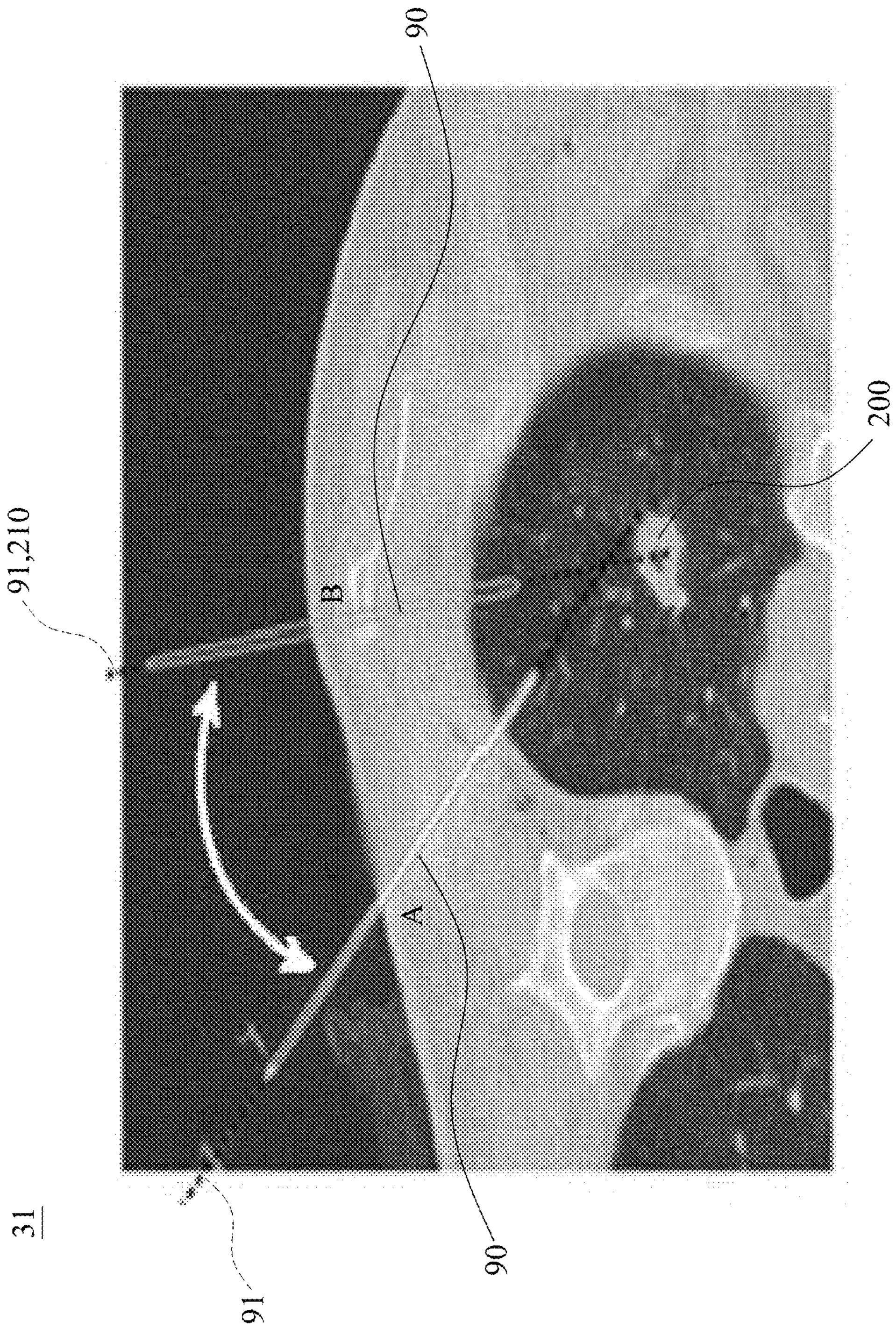
FIG. 5 is a schematic view of a single 2D image obtained by the diagnostic detection device of the present invention.
Figure 6:
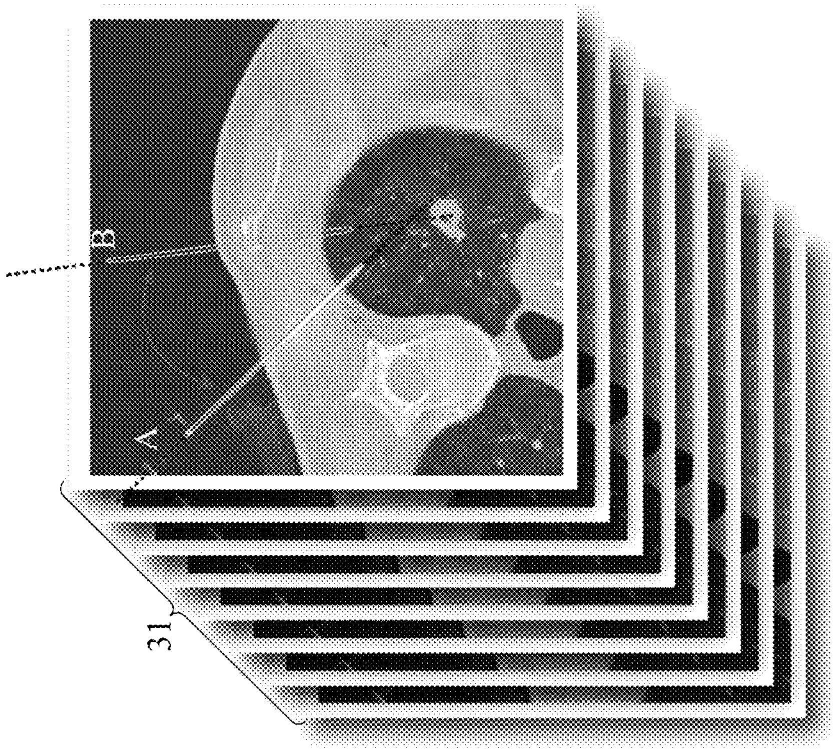
FIG. 6 is a schematic diagram of a plurality of 2Dl images obtained by the diagnostic detection device of the present invention and the image reconstruction module defining the spatial relationship between the cannula and the target.

As shown in FIGS. 5 to 7, in step S3 of the preferred embodiment, the image reconstruction module 11 receives the plurality 2D images 31, defines the spatial relationship between the cannula 90 and the target object 200 according to the plurality of 2D 31 and then a 3D image 111 is constructed. As shown in FIGS. 4, 5, 12, and 14, when the cannula 90 is at the first position A, an axis 91 of the cannula 90 is not aligned with an axis 210 of the target 200; that is to say, the cannula 90 and the target object 200 are not aligned, so the position of the cannula 90 needs to be adjusted. As shown in FIG. 5, FIG. 9, FIG. 12 and FIG. 13, when the cannula 90 is in the second position B, the axis 91 of the cannula 90 is aligned with the axis 210 of the target object 200; that is to say, the cannula 90 is aligned with the target object 200.

As shown in FIG. 3, and FIG. 9 to FIG. 12, in step S6 of the preferred embodiment, when the switching button 51 is activated, the foot pedal 50 sends a first switching signal 501 to the control device 10, and the control device 10, according to the first switch signal 501, controls the robot arm 20 to switch to the manual mode 21. As shown in FIG. 3, FIG. 13, and FIG. 14, in step S6 of the preferred embodiment, when the switching button 51 is inactivated, the foot pedal 50 sends a second switching signal 502 to the control device 10, and the control device 10, according to the second switch signal 502, controls the robot arm 20 to switch to the fixed mode 21.

Figure 12:
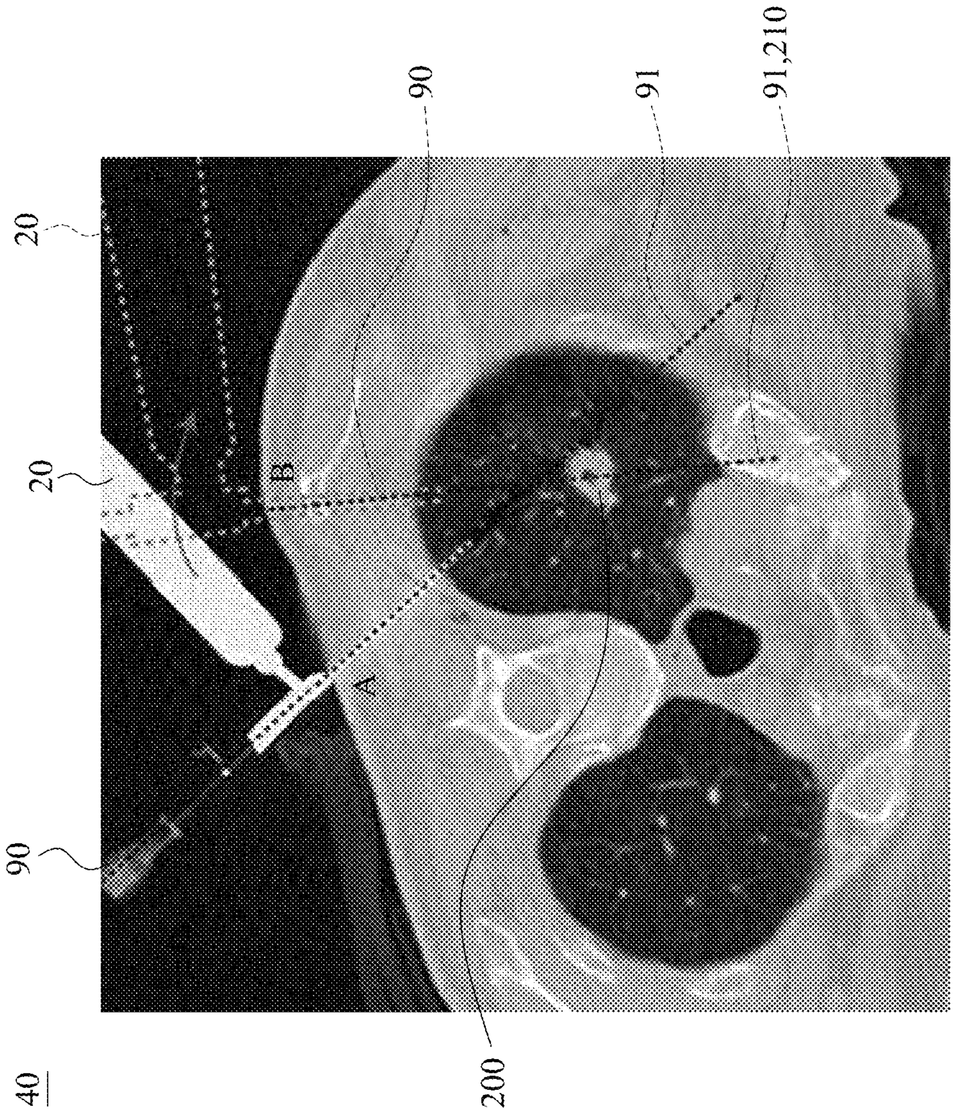
FIG. 12 is a schematic diagram of the screen displaying the movement trajectories of the robot arm and the cannula in the present invention.

In step S7 of the preferred embodiment, as shown in FIG. 3, FIG. 9, and FIG. 12, the control device 10 sets the path between the first position A and the second position B as the moving path 92 of the cannula 90, and the screen 40 displays the movement trajectories of the robot arm 20 and the cannula 90.

In step S8 of the preferred embodiment, as shown in FIG. 3, FIG. 9, and FIG. 13, in the fixed mode 22, when the first moving button 52 is activated and the second moving button 53 is not activated, the foot pedal 50 transmits a first moving signal 503 to the control device 10, the control device 10 controls the movement of the robotic arm 20 according to the first moving signal 503, and the robotic arm 20 drives the cannula 90 to move from the second position B to the first position A along the moving path 92, and the screen 40 displays the movement trajectories of the robot arm 20 and the cannula 90.

Figure 11:
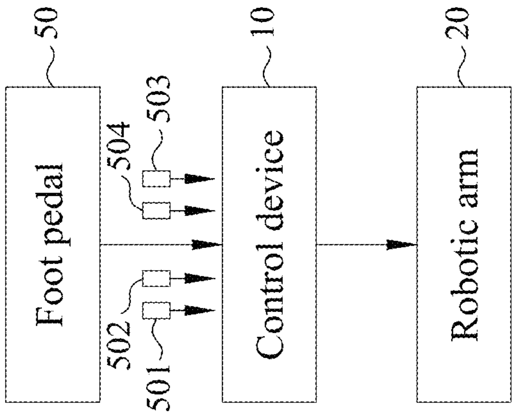
FIG. 11 is a structural schematic view of the foot pedal controlling the robotic arm through the control device of the present invention.

In step S9 of the preferred embodiment, as shown in FIG. 3, FIG. 11, and FIG. 14, in the fixed mode 22, when the second movement button 53 is activated and the first movement button 52 is not activated, the foot pedal 50 transmits a second moving signal 504 to the control device 10, the control device 10 controls the movement of the robotic arm 20 according to the second moving signal 504, and the robotic arm 20 drives the cannula 90 to move from the first position A to the second position B along the moving path 92, and the screen 40 displays the movement trajectories of the robot arm 20 and the cannula 90.

A practitioner may install a needle (not shown) on the cannula 90 before performing the above method. Therefore, in step S1, the needle is inserted into the first position A of the body of the patient 100; in steps S7-S9, the needle moves along with the cannula 90. In particular, after the cannula 90 is moved to the second position B, the needle is moved to the target object 200 in step S9.

The practitioner can also install a needle (not shown) on the cannula 90 after the cannula 90 moves to the second position B in step S9, and then insert the needle into the second position B of the patient's body. The needle moves to the target object 200.

As such, the present invention can provide a single practitioner to operate the entire surgical process such as puncture, scanning, and setting the moving path 92, and at the same time observe the position and movement trajectories of the robotic arm 20 and the cannula 90 through the screen 40, as well as step on the foot pedal 50 to control the robotic arm 20. Therefore, the practitioner can free up both hands to do things, save time and effort, achieve high operating efficiency, and save labor costs.

Furthermore, because the foot pedal 50 is small in size and placed on the ground, it will not affect the operation of the practitioners and does not take up space, so it is suitable to be placed on one side of the bed 80, and the screen 40 can be arranged on the other side of the bed 80. Therefore, the present invention can provide a practitioner standing on the side of the bed 80 to perform the surgical procedure without leaving the side of the bed 80 at all.

Figure 15:
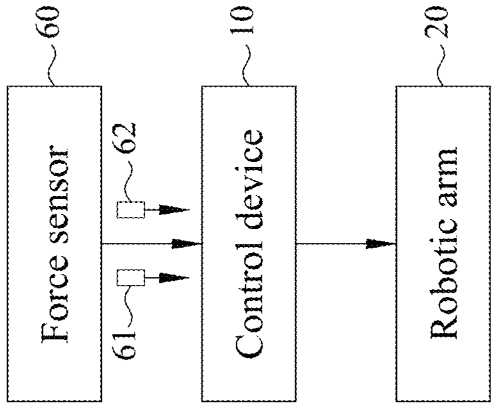
FIG. 15 is a block diagram of the force sensor controlling the robotic arm through the control device of the present invention.

As shown in FIG. 15, in a preferred embodiment, when the robotic arm 20 is switched to the manual mode 21 and a force sensor 60 is provided to sense that the robotic arm 20 is manually moved, the force sensor 60 transmits a first sensing signal 61 to the control device 10, and the control device 10 controls the robotic arm 20 to be manually moved according to the first sensing signal 61, so that the practitioner can move the robotic arm 20 at will to complete step S1 or step S7. Therefore, the present invention can activate the robotic arm 20 through the dual mechanism of the foot pedal 50 and the force sensor 60, and only then the robotic arm 20 is allowed to be moved manually, thereby improving the safety of operation.

As shown in FIG. 15, in a preferred embodiment, when the robotic arm 20 switches to the fixed mode 22 and the force sensor 60 senses that the robotic arm 20 is impacted by an external force, the force sensor 60 transmits a second sensing signal 62 to the control device 10, and the control device 10 controls the robotic arm 20 to stop moving according to the second sensing signal 62. Therefore, the present invention can sense whether the robotic arm 20 is hit by an external force in the fixed mode 22 through the force sensor 60, and immediately control the robotic arm 20 to stop moving, preventing the cannula 90 from moving on a deviated path 92 which will cause the needles on the cannula 90 to pull excessively on the patient's 100 wound.

Figure 16:
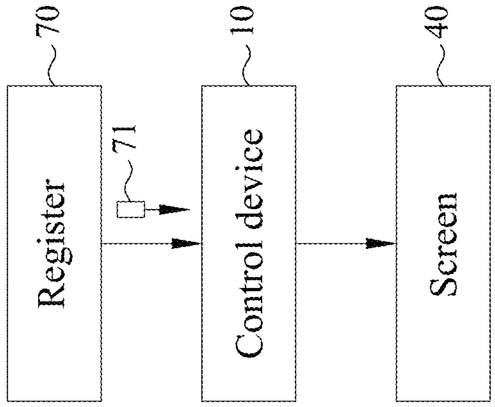
FIG. 16 is a block diagram of the register and the control device of the present invention to set the moving path and display the movement trajectories on the screen.

As shown in FIG. 16, in a preferred embodiment, when the robot arm 20 is switched to the manual mode 21, a register 70 is provided to store the real-time spatial position 71 of the robot arm 20, and the control device 10, according to the t real-time spatial position 71 provided by the register 70, recalculates the moving target position of the robotic arm 20 to set the moving path 92 of the cannula 90, and displays the movement trajectories of the robotic arm 20 and the cannula 90 on the screen 40. Therefore, the present invention can store the real-time position 71 of the robot arm 20 in the register 70, so as to recalculate the moving target position of the robot arm 20 and set the moving path 92 of the cannula 90, and uses the screen 40 to display the movement trajectories of the robot arm 20 and the cannula 90. The practitioner can observe the position of the cannula 90 and whether the moving path 92 is correct on the screen 40 while standing on the side of the bed 80 and controlling the robotic arm 20 by stepping on the foot pedal 50. In this way of operation, the practitioner can easily move the cannula 90 to the correct position at a step without repeated corrections, the operation efficiency is improved, and there is no need to additionally install an image capture device and employs another person to assist in the operation, so as to reduce the patient's radiation exposure and costs.

In a preferred embodiment, in the fixed mode 22, the moving speed of the robotic arm 20 is 0.2-1 cm per second. Therefore, the present invention can limit the movement of the robotic arm 20 at a low speed in the state of the fixed mode 22, which not only prevents the needles on the cannula 90 from being bent or broken, but also prevents the needles on the cannula 90 from excessively pulling on the patient's 100 wound.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A puncture guiding system, comprising:

a control device, having an image reconstruction module;

a robotic arm, electrically connected to the control device, having a manual mode and a fixed mode, and disposed with a cannula to be placed at a first position a patient's body:

a diagnostic detection device, electrically connected to the control device to scan the patient's body to obtain a plurality of two-dimensional (2D) images of the cannula and tissues near the first position; the image reconstruction module receiving the plurality of 2D images to construct a three-dimensional (3D) image:

a screen, electrically connected to the control device, for receiving and displaying the plurality of 2D images, 3D images, or a combination of both; and a foot pedal, electrically connected to the control device and comprising a switching button, a first moving button, and a second moving button;

wherein the control device controlling the robotic arm to switch to the manual mode or the fixed mode according to an actuation of the switching button;

wherein, in the manual mode, the robotic arm being manually moved to adjust the position of the cannula to a second position, and the control device setting a path between the first position and the second position as a moving path of the cannula;

wherein, in the fixed mode, the control device controlling the robotic arm to move according to an actuation of the first moving button to drive the cannula to move from the second position to the first position along the moving path, and the control device moving the cannula from the second position to the first position along the moving path according to an actuation of the second moving button; and wherein the screen displaying the movement trajectories of the robotic arm and the cannula.

2. The puncture guiding system according to claim 1, wherein the image reconstruction module defines a spatial relationship between the cannula and a target object according to the plurality of 2D images and constructs a 3D image: when the cannula is at the first position, an axis of the cannula and an axis of the target object are not aligned; when the cannula is at the second position, the axis of the cannula is aligned with the axis of the target object.

3. The puncture guiding system according to claim 1, wherein when the switching button is activated, the foot pedal transmits a first switching signal to the control device, and the control device controls the robotic arm to switch to the manual mode according to the first switching signal.

4. The puncture guiding system according to claim 1, wherein when the switching button is not activated, the foot pedal transmits a second switching signal to the control device, and the control device controls the robotic arm to switch to the fixed mode according to the second switching signal.

5. The puncture guiding system according to claim 1, wherein in the fixed mode, when the first moving button is activated and the second moving button is not activated, the foot pedal transmits a first moving signal to the control device, the control device controls the movement of the robotic arm according to the first moving signal, the robotic arm drives the cannula to move from the second position to the first position along the moving path, and the screen displays the movement trajectories of the robotic arm and the cannula.

6. The puncture guiding system according to claim 1, wherein in the fixed mode, when the second moving button is activated and the first moving button is not activated, the foot pedal transmits a second moving signal to the control device, the control device controls the movement of the robotic arm according to the second moving signa, the robotic arm drives the cannula to move from the first position to the second position along the moving path, and the screen displays the movement trajectories of the robotic arm and the cannula.

7. The puncture guiding system according to claim 1, further comprising a force sensor, disposed on the robotic arm and electrically connected to the control device: wherein, when the robotic arm switching to manual mode and the force sensor detecting that the robotic arm being manually moved, the force sensor sending a first sensing signal to the control device, and the control device controlling the robotic arm to be manually moved according to the first sensing signal.

8. The puncture guiding system according to claim 1, further comprising a force sensor, disposed on the robotic arm and electrically connected to the control device: wherein, when the robotic arm switching to the fixed mode and the force sensor detecting that the robotic arm being impacted by an external force, the force sensor sending a second sensing signal to the control device, and the control device controlling the robotic arm to stop moving according to the second sensing signal.

9. The puncture guiding system according to claim 1, further comprising a register disposed on the robotic arm and electrically connected to the control device; wherein, when the robotic arm switching to manual mode, the register stores a real-time spatial position of the robotic arm, the control device recalculating a moving target position of the robotic arm according to the real-time spatial position of the robotic arm provided by the register, so as to set the moving path of the cannula, and the screen displaying the movement trajectories of the robotic arm and the cannula.

10. The puncture guiding system according to claim 1, wherein the robotic arm has a moving speed of 0.2-1 cm per second in the fixed mode.

11. A puncture guiding method, comprising the following steps:

controlling a robotic arm to drive a cannula to be placed at a first position on a patient's body, the cannula being installed on the robotic arm;

providing a diagnostic detection device to scan the patient's body to obtain a plurality of 2D images of the cannula and tissues near the first position:

constructing a 3D image based on the plurality of 2D images: providing a screen to display the plurality of 2D images and 3D images, or any combination of both:

providing a foot pedal, the foot pedal comprising: a switching button, a first moving button, and a second moving button: according to the activation of the switching button, controlling the robotic arm to switch to a manual mode or a fixed mode:

in the manual mode, the robotic arm being manually moved to adjust the position of the cannula to a second position, and the path between the first position and the second position being defined as a moving path of the cannula, and the screen displaying the movement trajectories of the cannula and the robotic arm:

in the fixed mode, according to the activation of the first moving button, controlling the movement of the robotic arm to drive the cannula to move from the second position to the first position along the moving path, and the screen displaying the movement trajectories of the robotic arm and the cannula; and in the fixed mode, according to the activation of the second moving button, controlling the movement of the robotic arm to drive the cannula to move from the first position to the second position along the moving path, and the screen displaying the movement trajectories of the robotic arm and the cannula.

12. The puncture guiding method according to claim 11, wherein the image reconstruction module defines a spatial relationship between the cannula and a target object according to the plurality of 2D images and constructs a 3D image: when the cannula is at the first position, an axis of the cannula and an axis of the target object are not aligned; when the cannula is at the second position, the axis of the cannula is aligned with the axis of the target object.

13. The puncture guiding method according to claim 11, wherein when the switching button is activated, the foot pedal transmits a first switching signal to the control device, and the control device controls the robotic arm to switch to the manual mode according to the first switching signal.

14. The puncture guiding method according to claim 11, wherein when the switching button is not activated, the foot pedal transmits a second switching signal to the control device, and the control device controls the robotic arm to switch to the fixed mode according to the second switching signal.

15. The puncture guiding method according to claim 11, wherein in the fixed mode, when the first moving button is activated and the second moving button is not activated, the foot pedal transmits a first moving signal to a control device, the control device controls the movement of the robotic arm according to the first moving signal, the robotic arm drives the cannula to move from the second position to the first position along the moving path, and the screen displays the movement trajectories of the robotic arm and the cannula.

16. The puncture guiding method according to claim 11, wherein in the fixed mode, when the second moving button is activated and the first moving button is not activated, the foot pedal transmits a second moving signal to the control device, the control device controls the movement of the robotic arm according to the second moving signa, the robotic arm drives the cannula to move from the first position to the second position along the moving path, and the screen displays the movement trajectories of the robotic arm and the cannula.

17. The puncture guiding method according to claim 11, wherein when the robotic arm switches to manual mode and a force sensor is provided to detect that the robotic arm is manually moved, the force sensor sends a first sensing signal to a control device, and the control device controls the robotic arm to be manually moved according to the first sensing signal.

18. The puncture guiding method according to claim 11, wherein when the robotic arm switches to the fixed mode and a force sensor is provided to detect that the robotic arm is impacted by an external force, the force sensor sends a second sensing signal to the control device, and the control device controls the robotic arm to stop moving according to the second sensing signal.

19. The puncture guiding method according to claim 11, wherein when the robotic arm switches to manual mode, a register is provided to store a real-time spatial position of the robotic arm, the control device recalculates a moving target position of the robotic arm according to the real-time spatial position of the robotic arm provided by the register, so as to set the moving path of the cannula, and the screen displays the movement trajectories of the robotic arm and the cannula.

20. The puncture guiding method according to claim 11, wherein the robotic arm has a moving speed of 0.2-1 cm per second in the fixed mode.

* * * * *